(12) United States Patent
Phillips

(10) Patent No.: US 6,462,079 B2
(45) Date of Patent: Oct. 8, 2002

(54) PHARMACEUTICAL COMPOSITION AND METHOD OF USING THE SAME

(75) Inventor: Mark W. Phillips, Coconut Creek, FL (US)

(73) Assignee: Zetetic Research, Inc., Coconut Creek, FL (US)

( * ) Notice: Subject to any disclaimer, the term of this patent is extended or adjusted under 35 U.S.C. 154(b) by 0 days.

(21) Appl. No.: 09/999,545

(22) Filed: Oct. 23, 2001

(65) Prior Publication Data

US 2002/0061926 A1 May 23, 2002

Related U.S. Application Data

(62) Division of application No. 09/757,339, filed on Jan. 9, 2001.
(60) Provisional application No. 60/175,313, filed on Jan. 10, 2000.

(51) Int. Cl.⁷ .......................... A61P 31/04; A61P 31/12; A61P 31/10; A61P 31/18; A61P 31/20
(52) U.S. Cl. .................. 514/493; 514/643; 424/405; 424/423
(58) Field of Search ................ 514/643, 493, 514/894; 424/184.1, 405, 423

(56) References Cited

U.S. PATENT DOCUMENTS

| | | | |
|---|---|---|---|
| 3,594,468 A | 7/1971 | Saurino et al. | 424/25 |
| 4,021,537 A | 5/1977 | Saurino | 424/54 |
| 4,204,954 A | 5/1980 | Jacob | 210/59 |
| 4,263,278 A | 4/1981 | Saurino et al. | 424/75 |
| 4,283,421 A | 8/1981 | Ray | 424/317 |
| 4,321,277 A | 3/1982 | Saurino | 424/329 |
| 4,343,815 A | 8/1982 | Gitlitz | 424/288 |
| 4,464,398 A | 8/1984 | Sheets et al. | 424/329 |
| 4,684,663 A | 8/1987 | Plum et al. | 514/493 |
| 4,732,911 A | 3/1988 | Whitekettle et al. | 514/493 |
| 4,797,420 A | 1/1989 | Bryant | 514/643 |
| 4,832,744 A | 5/1989 | Imsgard et al. | 106/15.5 |
| 4,902,720 A | 2/1990 | Baldone | 514/642 |
| 4,914,132 A | 4/1990 | Donofrio et al. | 514/643 |
| 4,928,629 A | 5/1990 | Trampel | 119/1 |
| 4,998,984 A | 3/1991 | McClendon | 206/205 |
| 5,169,536 A | 12/1992 | Vasconcellos et al. | 210/691 |
| 5,336,305 A | 8/1994 | Staats | 106/18.32 |
| 5,417,968 A | 5/1995 | Staats | 424/78.07 |
| 5,444,094 A | 8/1995 | Malik et al. | 514/643 |
| 5,611,938 A | 3/1997 | Smolik et al. | 210/755 |
| 5,698,207 A | 12/1997 | Staats | 424/78.06 |

Primary Examiner—Edward J. Webman
Assistant Examiner—Helen Nguyen
(74) Attorney, Agent, or Firm—Pearne & Gordon LLP

(57) ABSTRACT

A pharmaceutical composition is provided for systemically treating a living mammal or avian. The composition preferably comprises an alkyl-dimethyl-benzyl-ammonium chloride, an alkyl-dimethyl-ethylbenzyl-ammonium chloride, and an organotin compound in a vehicle suitable for systemically treating a living mammal or avian of viral, bacterial, fungal infections and diseases, including HIV in humans.

30 Claims, No Drawings

PHARMACEUTICAL COMPOSITION AND METHOD OF USING THE SAME

RELATED APPLICATIONS

This application is a division of U.S. application Ser. No. 09/757,339, filed Jan. 9, 2001, now pending, which claims the benefit of U.S. Provisional Application No. 60/175,313, filed Jan. 10, 2000, the contents of which are incorporated by reference in their entirety.

FIELD OF THE INVENTION

The present invention is directed toward a pharmaceutical composition and a method of using the pharmaceutical composition to prevent and treat infections and diseases in mammals and avians.

BACKGROUND OF THE INVENTION

The present invention relates to a method for preventing or treating infection and disease in a mammal or avian caused by a virus or other infective or disease agent. More specifically, the invention relates to the administration of a pharmaceutical composition to a mammal.

Viruses are associated with a large number of infections and diseases in avians and mammals, such as man. Although modern medical science has developed some treatment techniques that are effective to prevent a particular disease, e.g., the polio vaccine, the art generally lacks a method by which a large number of different virus infections can be effectively prevented or treated.

Past treatments of various diseases caused by viruses have been largely ineffective. Accordingly, there is a strong need for a method that can effectively treat or prevent infections and diseases caused by viruses in a mammal or avian. Although quaternary ammonium compounds have been known in the art, for example as described in U.S. Pat. No. 4,902,720, the contents of which are hereby incorporated by reference in their entirety, the art has failed to provide an effective treatment for a wide variety of infections and diseases associated with a variety of viruses, bacteria, fungi, and other disease causing agents. The present invention is addressed to this need.

SUMMARY OF THE INVENTION

A pharmaceutical composition is provided for systemically treating a living mammal or avian, comprising a first quaternary ammonium compound, a second quaternary ammonium compound and an organometallic compound in a vehicle suitable for systemically treating a living mammal or avian. A method of using the composition is also provided.

DETAILED DESCRIPTION OF THE PREFERRED EMBODIMENTS OF THE INVENTION

As used herein, when a preferred range such as 5–25 is given, this means preferably at least 5 and, separately and independently, preferably not more than 25. Parts are parts by weight and percentages are weight percent unless otherwise indicated or apparent.

The pharmaceutical composition comprises a quaternary ammonium compound (A) (sometimes referred to herein as Compound A), a quaternary ammonium compound (B) (sometimes referred to herein as Compound B), and an organometallic compound. The quaternary ammonium compound (A), the quaternary ammonium compound (B), and the organometallic compound (C) are preferably present in the pharmaceutical composition in a ratio relative to each other of 5 parts quaternary ammonium compound (A) to 5 parts quaternary ammonium compound (B) to 2 parts organometallic compound, less preferably as shown in the following formulation.

Preferably, quaternary ammonium compound (A) and quaternary ammonium compound (B) are present in the pharmaceutical composition in a ratio relative to each other of 1 part quaternary ammonium compound (A) to 1 part quaternary ammonium compound (B), less preferably 3 to 8 parts quaternary ammonium compound (A) to 2 to 7 parts quaternary ammonium compound (B), still less preferably 0.5 to 9.5 parts quaternary ammonium compound (A) to 0.5 to 9.5 parts quaternary ammonium compound 1 (B). Preferably, the quaternary ammonium compound (A) and organometallic compound are present in the pharmaceutical composition in a ratio relative to each other of 50 parts quaternary ammonium compound (A) to 2 parts organometallic compound, less preferably 25 to 75 parts quaternary ammonium compound (A) to 1 to 10 parts organometallic compound, still less preferably 10 to 100 parts quaternary ammonium compound (A) to 0.5 to 20 parts organometallic compound.

The pharmaceutical composition may be prepared in a stock solution using sterilized water. The table below sets forth a preferred formulation and less preferred formulations of the stock solution. All figures listed in the following table are in weight percent.

|  | Preferred | Less Preferred | Less Preferred | Less Preferred | Less Preferred | Less Preferred |
|---|---|---|---|---|---|---|
| Compound A | 5 | 4–6 | 3–8 | 2–25 | 1–50 | 0.001–95 |
| Compound B | 5 | 3–7 | 1–10 | 0.5–25 | 0.05–50 | 0.001–95 |
| Organometallic compound | 2 | 1.5–2.5 | 1–3 | 0.75–3.5 | 0.5–4 | 0.001–5 |
| Sterile Water | 88 | 84.5–91.5 | 79–95 | 46.5–96.75 | 40–98.45 | 0.0–99.997 |

Alternatively the stock solution can be 5 g Compound A, 5 g Compound B, and 200 mg organometallic compound in 1 L sterile water.

Dilution of the stock solution creates a use solution. In the use solution, Compound A is preferably present at 0.5–0.00005 weight percent, more preferably 0.05–0.0005 weight percent, most preferably about 0.005 weight percent. Compound B is preferably present in the use solution at 0.5–0.00005 weight percent, more preferably 0.05–0.0005 weight percent, most preferably 0.005 weight percent. The use solution preferably contains 0.02–0.000002 weight percent of the organometallic compound, more preferably 0.002–0.00002 weight percent, most preferably 0.0002 weight percent.

The quaternary ammonium compound (A) is preferably a quaternary ammonium halide compound, more preferably an alkyl-dimethyl-benzyl-ammonium chloride. Still more preferably, the quaternary ammonium compound (A) is n-alkyl($60\%C_{14}$, $30\%C_{16}$, $5\%C_{12}$, $5\%C_{18}$)-dimethyl-benzyl-ammonium chloride.

The quaternary ammonium compound (B) is preferably a quaternary ammonium halide compound, more preferably an alkyl-dimethyl-ethylbenzyl-ammonium chloride. Still more preferably, the quaternary ammonium compound (B) is n-alkyl(68%$C_{12}$, 32%$C_{14}$)-dimethyl-ethylbenzyl-ammonium chloride.

The organo-metallic compound is preferably an organotin compound, more preferably a triorganotin compound. Still more preferably the organo-metallic compound is bis(tri-n-butyltin)oxide, or a water-soluble and/or water-dispersable ester of bis(tri-n-butyltin)oxide. Still more preferably, the organo-metallic compound is bis(tri-n-butyltin)oxide. Among the water-soluble and/or water dispersable esters of bis(tri-n-butyltin)oxide, tri-n-butyltin benzoate and tri-n-butyltin-butyrate are preferred.

Less preferably, the organo-metallic compound may be another organo-metallic compound, such as an organozinc compound, an organosilver compound, or an organogold compound.

A use solution of the pharmaceutical composition is prepared from the stock solution using a pharmaceutically effective carrier or diluent. The diluent may be lactated ringers, ringers, an NaCl solution, Normasol R, Normasol, or a 5% dextrose solution. The use solution is preferably prepared using a dilution ratio of diluent to stock solution of about 10,000:1 to 1:1, more preferably about 10,000:1 to 10:1, more preferably about 10,000:1 to 100:1, more preferably about 1,000:1 to 100:1, still more preferably about 1,000:1.

With a dilution ratio of 1,000:1 the pharmaceutical composition has a preferred formulation of 0.005% quaternary ammonium compound (A), 0.005% quaternary ammonium compound (B), and 0.002% (less preferably 0.0002%) organometallic compound.

The pharmaceutical composition is systemically administered to a mammal or avian infected with a virus. The mammals to which the pharmaceutical composition may be administered includes humans, equines, canines, felines, porcines, bovines, and other non-human mammals. The systemic administration of the pharmaceutical composition may be used to treat or prevent infections and diseases caused by viruses, bacteria, fungus and other microbes, and to treat or prevent the other diseases or conditions described herein.

The pharmaceutical composition may be systemically administered to a mammal or avian intravenously, subcutaneously, orally, intra-nasally, intramuscularly, or through nebulization.

The pharmaceutical composition can be administered to a mammal or avian in a dosage effective to produce an anti-viral effect with respect to the virus. The pharmaceutical composition can also be administered to a mammal or avian in a dosage effective to inhibit viral function of the virus. Of course, the same administration of the pharmaceutical composition to a mammal or avian can simultaneously achieve both of these effects.

The pharmaceutical composition can be administered in a therapeutically-effective dosage to the mammal or avian. Generally, the dosage of the pharmaceutical composition to be administered to a mammal or avian is 1 cc, less preferably 0.5–2 or 0.3–4 cc, of the pharmaceutical composition (with a stock dilution ratio of 1,000:1) per kilogram of the mammal or avian being treated over a 24 hour period, at a slow infusion rate. This dosage of the pharmaceutical composition is administered to the subject for a period of time generally lasting from 1 to 14 days.

EXAMPLES

In the following examples the pharmaceutical composition which was tested was 5 g n-alkyl-dimethyl-benzyl-ammonium chloride with 5 g n-alkyl-dimethyl-ethylbenzyl-ammonium chloride and 200 mg tri-n-butyltin-benzoate in 1 L sterile water (stock solution) which was diluted with lactated ringers solution to make a use dilution of 0.005% n-alkyl-dimethyl-benzyl-ammonium chloride, 0.005% n-alkyl-dimethyl-ethylbenzyl-ammonium chloride and 0.0002% tri-n-butyltin-benzoate which was dosed at the rate of 1 cc per kilogram of subject body weight per 24 hours, continued for 1–14 days (hereinafter Standard Dosage).

Animal tests have indicated that the pharmaceutical composition is effective in treating Equine Infection Anemia (EIA), or swamp fever, in horses and ponies. Tests also indicate that the composition is effective against Feline Leukemia Virus (FELV) in cats and Bovine Leukemia Virus (BLV) in bovines. Tests in psittacines (parrots and related avians) indicate effectiveness in treating Papovavirus, and Avian Pox.

These animal tests indicate that the pharmaceutical composition has function as a broadband anti-viral agent. In addition to the anti-viral effect seen in the above-mentioned tests, the pharmaceutical composition correlated with positive treatment outcomes in trial studies of cats exhibiting Feline Lymphosarcoma and cows and calves with malignant Bovine Lymphoma. The composition furthermore correlated to positive outcomes in trial treatment of psittacines exhibiting Aspergillosis. These trials indicate that the composition is effective not only as an anti-viral but also against tumors and systemic fungal infection. Furthermore, the effectiveness of the pharmaceutical composition at low concentrations. indicates that it acts as an immune system adjuvant, stimulating production of antibodies. Thus the composition may act synergistically with partially-protective pre-existing vaccines, which also act as immune system adjuvants.

In addition to the initial animal trial data, the pharmaceutical composition was tested in vitro against four strains of type 2 and type 1 herpes virus in culture to determine the minimum effective pharmaceutical concentrations and evaluate possible mechanisms of the anti-viral function. The tests indicated that the anti-viral effect was not due to generalized cytotoxicity or induction of interferon production.

Toxicity testing in murines indicated that the pharmaceutical composition became toxic at levels approximately 30 to 100 times the therapeutic dose of 1 cc of the pharmaceutical composition (with a stock dilution ratio of 1,000:1) per kilogram of the mammal or avian being treated over a 24 hour period. In the test, this ratio worked out to 10 mg (dry weight measure) of the pharmaceutical composition per kilogram mass of the test subject. A further tissue irritation study carried out by administering the diluted composition to rabbits in the eye resulted in no reaction, irritation or corneal opacity.

Following the animal tests, studies were performed to determine the effectiveness of the pharmaceutical composition in treating disease in humans. One hundred-twenty-seven individuals infected with HIV were treated intravenously with the pharmaceutical composition at the Standard Dosage set forth above. Considering one days's administration of the pharmaceutical composition at the Standard Dosage as a single treatment, about 70% of the patients received a single treatment, while about 17% received from 2 to 5 treatments, about 6% received from 6 to 14 treatments, and about 7% received 15 or more treatments.

Levels of HIV-1 and P-24 antigens (two common indicators of the level of infection) were measured in two subsets of these patients both before and one week after the treatment. The mean HIV-1 antigen level measured fell from 244.4 micrograms/ml to 132.9 micrograms/ml while the mean P-24 antigen measured fell from 941 micrograms/ml to 168 micrograms/ml. Of the group tested for HIV-1 antigen, three of nine in one subset and one of five in the other subset produced nondetectible levels of antigen one week after treatment.

HIV viral loads were also measured by PCR (polymerase chain reaction) in four patients both before and one week after treatment, showing a 48.5% reduction in mean HIV levels (from 217,003 to 111,732 copies/ml). Hepatitis C (HCV) viral load was also measured for several patients who were co-infected with both HCV and HIV. In one of these patients who received multiple treatments with the pharmaceutical composition the level of HCV fell to zero following treatment. Among the four patients whose HCV levels were measured using PCR, the mean HCV viral load fell 97.6% (from 2,441,363 to 59,281 copies/ml). In connection with treating HCV-infected patients it was noted that liver enzymes SGOT and SGPT fell from elevated to normal levels following treatment.

Levels of Beta 2 Microglobulin, an indicator of cell breakdown, were also measured in 19 of the patients following treatment with the pharmaceutical composition. Mean levels decreased, indicating that the pharmaceutical composition was not toxic as administered to the patients.

A separate trial showed reduction or elimination of P. chlamydia from the blood of several patients following treatment with the pharmaceutical composition.

In a trial involving two patients exhibiting symptoms of chronic fatigue syndrome and having abnormally low populations of Natural Killer (NKHT3−) lymphocytes, NKH T3− and NKH T3+ levels returned to normal levels following a single treatment as defined above. The patients also indicated that their level of fatigue was reduced. This effect lasted for approximately two months, following which time NKH T3 counts returned to pre-treatment levels.

These trials indicate that the pharmaceutical composition has broad-band systemic anti-viral, anti-bacterial, anti-fungal, and immune adjuvant properties. As such the composition can be used to treat abscesses; acne; adenoviruses; AIDS; HIV; arbovirus diseases; aspergillosis; avian pox; bacteremia; benzodiazepam withdrawal; brucellosis; candidiasis; cancer; cellulitis; chlamydia; clostridia; cold sores; coronary artery disease; coryza; common cold rhinoviruses; common human skin fungi; common warts; cutaneous abscesses; cytomegalovirus diseases; delayed T-cell hypersensitivity reaction; dermatomycoses; dermatophyte infections; envelope virus infections; Epstein-Barr virus; equine infectious anemia; fungal infections; gram negative bacteria; gram positive bacteria; halitosis; herpes types A & B; HHV6; hypo-pituitarism; hepatitis (A, B, & C); hypophysitis; human retroviruses, including but not limited to HIV, HTLV1 and HTLV II; influenza and parainfluenza viruses; Kaposils sarcoma; lymphadenitis; meningitis; molluscum contagiosum; mycoses fungoides; mycobacterium diseases, including tuberculosis and leprosy; necrotizing subcutaneous infections; neuropathy (AIDS associated); non-envelope viruses; oral candidiasis; oral hairy leukoplasia; osteomyelitis; otitis externa; Papova virus; peripheral neuropathy (AIDS associated); pneumonia, particularly P. chlamydia; prevention of HIV infection after contaminated needle stick; prostatitis (bacterial); pseudomonas infections; psittacine beak and feather disease; rhinovirus; salmonella; sinusitis; staphlococeal infections; streptococcal infections; thrush; tinea; tuberculosis; vaginal yeast infections; and miscellaneous wounds, including use as burn therapy when combined with an emollient.

This list is not meant to be limiting, but rather illustrative of diseases to be treated with the inventive composition. Other infections and diseases in human and non-human mammals and avians can be treated with the pharmaceutical composition of the present invention, using the teachings herein.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of treating an infection or disease in a living mammal or avian comprising the stop of systemically treating said living mammal or avian with a therapeutically-effective amount of a pharmaceutical composition comprising a first quaternary ammonium compound, a second quaternary ammonium compound and an organometallic compound in a vehicle effective for systemically treating a living mammal or avian.

2. A method according to claim 1, wherein said first quaternary ammonium compound is an alkyl-dimethyl-benzyl-ammonium chloride, said second quaternary ammonium compound is an alkyl-dimethyl-ethylbenzyl-ammonium chloride, and said organometallic compound is selected from the group consisting of organotin compounds, organozinc compounds, organosilver compounds, and organogold compounds.

3. A method according to claim 1, wherein said first quaternary ammonium compound is n-alkyl($60\%C_{14}$, $30\%C_{16}$, $5\%C_{12}$, $5\%C_{18}$)-dimethyl-benzyl-ammonium chloride, said second quaternary ammonium compound is n-alkyl ($68\%C_{12}$, $32\%C_{14}$) -dimethyl-ethylbenzyl-ammonium chloride, and said organometallic compound is bis(tri-n-butyltin)oxide or a water-soluble or-water-dispersable ester thereof.

4. A method according to claim 1, wherein said composition is about 0.5 to 0.00005 weight percent said first quaternary ammonium compound, about 0.5 to 0.00005 weight percent said second quaternary ammonium compound, and about 0.02 to 0.000002 weight percent said organometallic compound.

5. A method according to claim 3, wherein said composition is about 0.5 to 0.00005 weight percent said first quaternary ammonium compound, about 0.5 to 0.00005 weight percent said second quaternary ammonium compound, and about 0.02 to 0.000002 weight percent said organometallic compound.

6. A method according to claim 3, wherein said composition is about 0.005 weight percent said first quaternary ammonium compound, about 0.005 weight percent said second quaternary ammonium compound, and about 0.0002 weight percent said organometallic compound.

7. A method according to claim 3, wherein the weight ratio of said first quaternary ammonium compound to said second quaternary ammonium compound is from 10:1 to 1:10 and the weight ratio of said first quaternary ammonium compound to said organometallic compound is from 500:2 to 50:20.

8. A method according to claim 1, further comprising a step of systemically treating said living mammal or avian with a therapeutically acceptable adjuvant in combination with said pharmaceutical composition.

9. A method according to claim 8, wherein said therapeutically acceptable adjuvant is a vaccine.

10. A method according to claim 1, wherein said treating step is a step of treating a viral infection or a viral disease.

11. A method according to claim 1, wherein said treating step is a step of treating a bacterial infection or a bacterial disease.

12. A method according to claim 1, wherein said treating step is a step of treating a fungal infection or a fungal disease.

13. A method according to claim 1, wherein said treating step is a step of treating HIV or AIDS in a human.

14. A method according to claim 1, wherein said treating step is a step of treating Equine Infectious Anemia in an equine.

15. A method according to claim 1, wherein said treating step is a step of treating Feline Leukemia Virus, or Feline Lymphosarcoma in a feline.

16. A method according to claim 1, wherein said treating step is a step of treating Bovine Leukemia Virus or Bovine Lymphoma in a bovine.

17. A method according to claim 1, wherein said treating step is a step of treating Papovavirus, Avian Pox, or Aspergillosis in an avian.

18. A method according to claim 1, wherein said treating step is a step of treating Chronic Fatigue Syndrome in a human.

19. A method according to claim 1, wherein said treating step is a step of treating a Hepatitis C viral infection in a human.

20. The method of claim 1, wherein said treating step is a step of treating hepatitis A, hepatitis B, or hepatitis C in a human.

21. The method of claim 1, wherein said treating step is a step of treating chlamydia in a human.

22. The method of claim 1, wherein said treating step is a step of treating cytomegalovirus disease in a human.

23. The method of claim 1, wherein said treating step is a step of treating Epstein-Barr viral infection in a human.

24. The method of claim 1, wherein said breathing step is a step of treating herpes type A or herpes type B in a human.

25. The method of claim 1, wherein said treating step is a step of treating HTLV I or HTLV II in a human.

26. The method of claim 1, wherein said treating step is a step of treating Papova virus in a human.

27. The method of claim 1, wherein said treating step is a step of treating psittacine beak and feather disease in an avian.

28. The method of claim 1, wherein said treating step is a step of treating staphylococcal infection in a human.

29. The method of claim 1, wherein said treating step is a step of treating streptococcal infection in a human.

30. The method of claim 1, wherein said treating step is a step of treating tuberculosis in a human.

* * * * *

UNITED STATES PATENT AND TRADEMARK OFFICE
CERTIFICATE OF CORRECTION

PATENT NO. : 6,462,079 B2
DATED : October 8, 2002
INVENTOR(S) : Mark W. Phillips It is certified that error appears in the above-identified patent and that said Letters Patent is hereby corrected as shown below:

Column 2,
Line 16, after "compound" delete -- 1 --.

Column 3,
Line 44, delete "intramuscularly," and insert therefore -- intra-muscularly, --.

Column 4,
Line 30, delete "tions." and insert therefore -- tions --.

Column 6,
Line 23, delete "stop" and insert therefore -- step --.

Signed and Sealed this

Eleventh Day of March, 2003

JAMES E. ROGAN
*Director of the United States Patent and Trademark Office*